United States Patent [19]

Bridges

[11] 4,353,696

[45] Oct. 12, 1982

[54] VIBRATING DENTAL TOOL DEVICE AND METHOD

[76] Inventor: Byron K. Bridges, 110 Church St., Greer, S.C. 29651

[21] Appl. No.: 281,984

[22] Filed: Jul. 10, 1981

[51] Int. Cl.³ .............................................. A61C 3/06
[52] U.S. Cl. .................................. 433/125; 433/166; 433/119; 433/218
[58] Field of Search ................. 433/125, 166, 51, 142, 433/118, 119, 218

[56] References Cited

U.S. PATENT DOCUMENTS 2,990,616  7/1961  Balamuth et al. .................. 433/119
4,110,908  9/1978  Cranston ............................. 433/125

*Primary Examiner*—Robert Peshock
*Attorney, Agent, or Firm*—Dority & Flint

[57] ABSTRACT

A dental tool device and method is disclosed by which a smooth beveled surface may be formed on a shoulder of a tooth for receiving a crown fitting so that the joint therebetween is concealed as lying substantially below the gum-line and a solid seal is formed between the tooth and crown. The device includes a vibrating tool A having a shank 44 and contoured portion 46 which includes a contoured surface 48. Surface 48 is contoured and includes a coating 50 of diamond grit so as to form a smooth beveled surface 18 during vibration to finish a previously ground shoulder 14 in accordance with the invention. Tool A is adapted for attachment as an insert 34 into the handle 32 of a conventional ultrasonic dental instrument 30.

17 Claims, 5 Drawing Figures

VIBRATING DENTAL TOOL DEVICE AND METHOD

BACKGROUND OF THE INVENTION

The invention relates to a method and dental tool device for performing dental crown work. The tool may be adapted to the handle of a conventional dental ultrasonic vibrating instrument and includes a contoured surface having an abrasive diamond grit thereon which forms a beveled surface on a previously ground portion of the tooth by means of vibratory motion. The tool terminates in a smooth tip so as to protect the gum when vibrating below the gum-line.

Heretofore, various rotary tools have been utilized to grind a tooth for the fitting of a crown. However, if the tooth is ground below the line of the gum, cutting or damaging of the gum normally occurs. If the grinding stops short of or at the gum-line or if a cut gum shrinks upwardly, a joint line between the crown fitting and the tooth is exposed adversely affecting the cosmetic appearance of the crown work. Furthermore, a tooth ground by a conventional rotary tool usually results in a "ditched" out and wavy tooth surface due to uneven pressure and thus is generally not smooth. This results in gaps between the crown fitting. Bacteria can leak into these areas and become entrapped leading to decay.

Accordingly, an important object of the present invention is to provide a method and dental tool for performing dental crown work which forms a joint on a tooth lying below the gum-line which is accomplished without damaging or cutting the gum.

Still another important object of the present invention is to provide a dental tool device for performing dental crown work which vibrates and may be utilized below the line of the gum without the probability of cutting the gum.

Still another important object of the present invention is to provide a dental tool having a contoured surface which forms a generally smooth beveled surface on a tooth devoid of ditched areas providing a solid seal between the crown and tooth.

SUMMARY OF THE INVENTION

The above objectives are accomplished according to the present invention by providing a dental tool which may be utilized with an ultrasonic dental instrument adapted as an insert fit in a handle of such apparatus. The dental tool includes a shank portion connected to the insert from which extends a contoured portion having grit which forms a beveled surface on the tooth having a lower edge substantially below the gum-line. The contoured surface terminates in a smooth tip such as to avoid damage or cutting to the gum when vibrating below the gum-line and provides a smooth surface. Thus, a joint between the tooth and the crown is below the line of the gum improving cosmetic appearance and the crown is sealed solidly on the tooth. The method includes abrading a shoulder of a tooth, which has previously been ground with a rotary tool, with a vibrating tool to bevel the shoulder forming a lower edge substantially below the gum-line facilitating a concealed crown joint and a smooth surface receiving the crown fitting.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 2A is a sectional view taken along line 2A—2A of FIG. 2.

DESCRIPTION OF A PREFERRED EMBODIMENT

Figure 3:
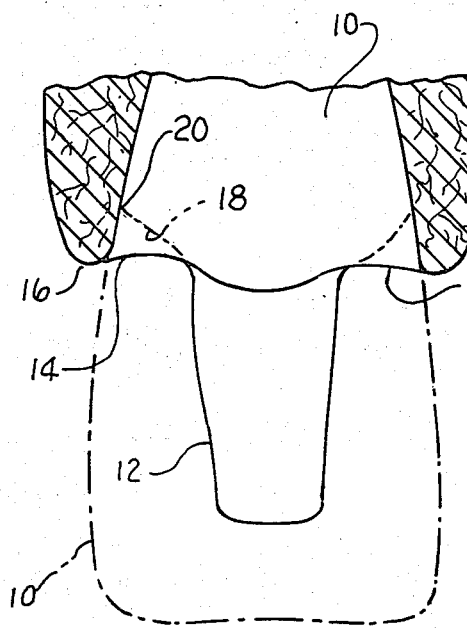
FIG. 3 is a schematic diagram of a tooth which has been ground away by means of a conventional method and rotating tool with the surface of the tooth shown in dotted lines being formed in accordance with the present method and dental tool device.

Referring now to the drawing, a method and dental tool for performing dental crown work on a tooth to improve the cosmetic appearance is disclosed wherein the method involves grinding a tooth shown in dash lines at 10 down to a central core 12 by means of a conventional rotary crown grinding tool which leaves a ground shoulder surface 14 appearing at or near the level of the gum-line 16 (FIG. 3). This may be done with any conventional diamond burr rotary grinding tool. Further rotary grinding is generally undesirable due to excessive cutting and damaging of the gum. The shoulder surface 14 includes "wavy" or "ditched" out areas (not shown).

In accordance with the method of the present invention, the ground shoulder 14 is abraded with a vibrating tool, designated generally as A, to form a generally smooth beveled surface shown in dotted lines 18 having a lower edge 20 which is well below that of the gum-line 16 of gum 22. Thus, surface 14 is finished in a smooth surface devoid of wavy or ditched areas. The joint 24 between the crown 26, which may be seen in dash lines in FIG. 4, and tooth 10 is concealed as lying substantially below the gum-line 16.

Figure 1:
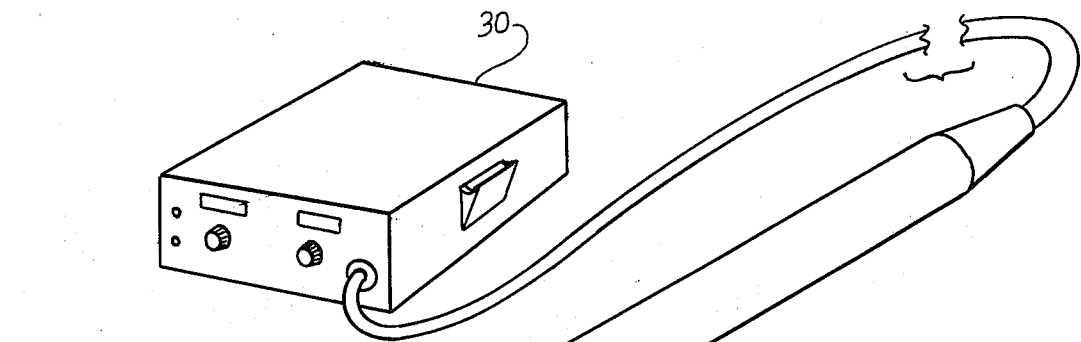
FIG. 1 is a perspective view illustrating a dental tool device for performing dental crown work constructed according to the present invention and is utilized with ultrasonic vibrating apparatus.

The method according to the present invention may be carried out by apparatus illustrated in FIG. 1 which includes a source 30 of ultrasonic vibration which may be any suitable ultrasonic dental instrument such as a Sonitron instrument manufactured by Simplified Systems, Inc., Miami Beach, Florida, having a frequency of twenty-five thousand Hertz at the tip. The ultrasonic instrument 30 typically includes a handle portion 32 in which an insert 34 is fitted. Water is delivered through a conduit 36 carried by the handle portion 32 to cool the grinding or abrading tool and work surface. In accordance with the present invention, a tool socket portion 38 is connected to the insert 34, which may be a conventional insert, for adapting a tool device A to the handle portion 32 and thus the source of ultrasonic vibration.

Connection may be had in any suitable manner such as soldering or welding. The tool socket 38 includes an outer metallic sleeve 40 and an inner plastic sleeve 42. Sleeve 40 has a threaded interior and sleeve 42 a threaded exterior whereby sleeve 42 is screwed into sleeve 40 by means of a suitable chuck.

The vibrating dental tool A constructed according to the present invention includes a shank portion 44 adapted to be pressed fitted within the plastic sleeve 42, and preferably, to be frictionally rotatable therein for purposes that will become more fully apparent. Carried by the shank portion 44 is a contoured portion 46 which includes contoured surface means 48 for forming a beveled surface on the tooth having an abrasive grit 50 carried thereon which is preferably a fine diamond grit. The tip of the tool terminates in a smooth portion 52 which will be next adjacent the gum during operation. Likewise, the surface 54 may also be smooth to terminate the cut line of abrading surface 48. The remainder of the tip 56 is preferably formed so as to be smooth. Thus, owing to the configuration of tool A and the vibrating rather than rotary operation, the likelihood of gum cutting or damage during finishing of tooth 10 is reduced or virtually eliminated. A smooth surface 18 is provided for receiving and solidly sealing against the crown 26.

Figure 2:
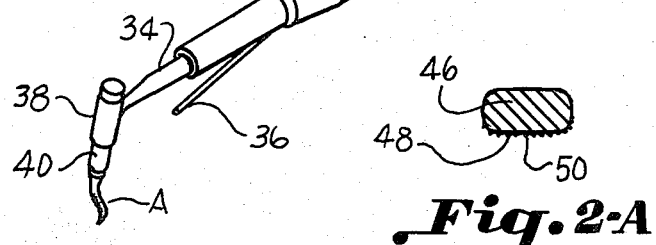
FIG. 2 is a side elevation illustrating a dental tool device constructed according to the present invention.
Figure 2:
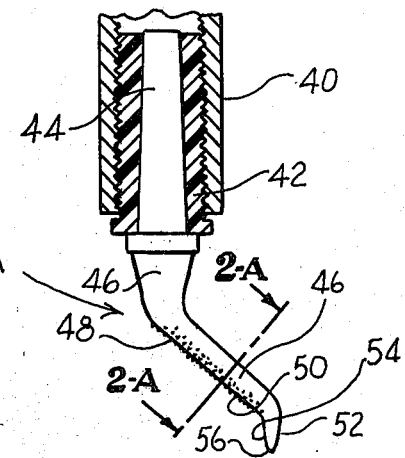

The contoured surface 50 is inclined to the shank portion 44 and is contoured so that when placed on shoulder 14, a beveled surface such as illustrated at 18 will result. The contoured surface 50 is preferably flat, as best seen in FIG. 2A, such as to afford a wider abrading surface facilitating formation of the beveled surface 18.

Figure 4:
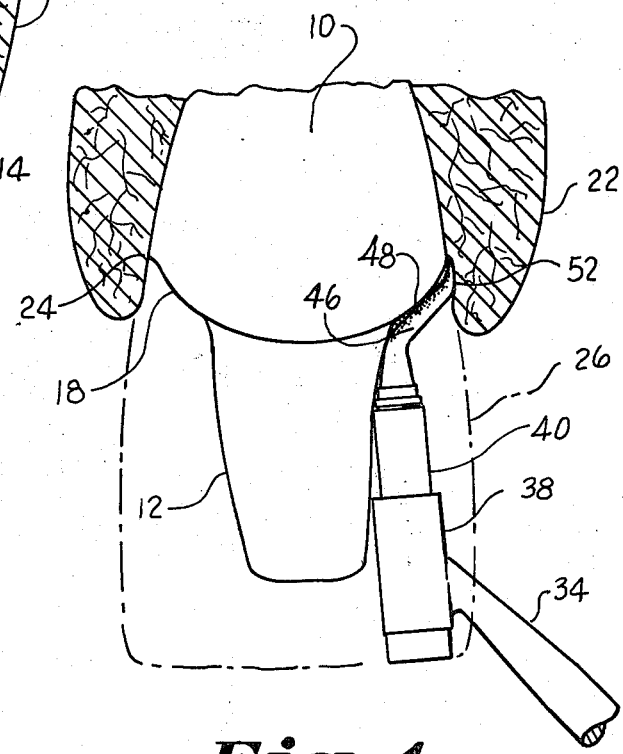
FIG. 4 is a schematic view illustrating a gum and tooth in section which has been abraded and beveled in accordance with the method and device of the present invention.

In use, the dental tool will assume a position relative to the core 12 and handle portion 32 as best seen in FIG. 4. As the tool A vibrates around shoulder 14, it is an expedient to the operation and method that the tool A be free to turn in the sleeve 42 relative to outer sleeve 40. In this manner, the tooth shoulder may be followed quite readily with least obstruction from the core or handle portion and expedites formation of a smooth surface.

Thus, it can be seen that an advantageous method and tool device for use in dental crown work can be had according to the present invention wherein a tooth may be abraded below the gum-line in order that a joint of crown fitting will lie concealed below the gum-line providing a pleasing and cosmetically appearing crown.

While a preferred embodiment of the invention has been described using specific terms, such description is for illustrative purposes only, and it is to be understood that changes and variations may be made without departing from the spirit or scope of the following claims.

What is claimed is:

1. A dental tool device for performing dental crown work on a tooth and improving the sealing and cosmetic appearance thereof which may be utilized with ultrasonic dental apparatus for ultrasonically vibrating said tool device, wherein said tool device comprises:
a shank portion adapted for connection to an operating handle portion of said ultrasonic dental apparatus;
contoured surface means carried by said shank portion having abrasive means carried thereon abrading said tooth during vibration; and
said contoured surface and abrasive means providing means forming a gnerally smooth beveled surface on said tooth;
whereby an edge of said surface may be formed to lie below the gum providing a concealed joint between said tooth and crown work and said crown fitting seals solidly on said smooth surface.

2. The apparatus of claim 1 wherein said contoured surface means is generally flat.

3. The apparatus of claim 1 wherein said dental tool terminates in a smooth surface on a side facing said gum when in operation.

4. The apparatus of claim 1 wherein said dental tool terminates in a smooth surface on a side facing said gum and on a side which carries said abrasive.

5. The apparatus of claim 1 wherein said contoured means includes a portion of said tool extending away from said shank protion and being thereto.

6. The apparatus of claim 5 including a tip portion terminating said tool inclined and adjacent to said contoured portion, said tip portion being generally smooth on a side facing said gum when in use.

7. The apparatus of claim 1 wherein said abrasive means includes diamond grit material.

8. The apparatus of claim 2 wherein said contoured surface means is inclined to said shank portion.

9. A dental tool device of the type held by a tool handle for performing dental crown work and for improving the sealing and cosmetic appearance thereof, said tool device being operable upon vibration to abrade a shoulder of a tooth ground by a rotary tool during said crown work and comprises:
a shank portion adapted for connection to a tool handle;
contoured means carried by said shank portion having abrasive means carried thereon abrading said tooth during vibration of said tool device; and
said contoured surface and abrasive means providing means abrading said shoulder forming a generally smooth beveled surface on said tooth;
whereby an edge of said surface may be formed to lie below the gum providing a concealed joint between said tooth and crown fitted thereon and a more solid seal may be formed between said abraded surface and crown fitting.

10. The device of claim 9 wherein said contoured means is generally flat.

11. The device of claim 9 wherein said dental tool terminates in a smooth surface on a side facing said gum when in use.

12. The device of claim 9 wherein said dental tool terminates in a smooth surface on a side facing said gum and on a side which carries said abrasive.

13. The device of claim 9 wherein said abrasive means includes diamond grit material carried on said contoured surface means.

14. A method of cutting away a tooth for fitting of a dental crown of the type wherein the tooth is ground to a shoulder leaving a central core over which the crown is fitted, wherein the improvement comprises:
abrading said shoulder of said tooth with a vibrating tool forming a generally beveled surface having a lower edge substantially below said gum-line so that a joint between said tooth and crown is fitted thereon, said surface being generally smooth to provide a more solid seal for said crown.

15. The method of claim 14 including:
providing a dental tool which is vibrated having a shank portion; and
providing a vibrating dental tool having a shank portion adapted for connection to a source of ultrasonic vibration and a contoured portion carried by said shank portion having an abrasive carried thereon for abrading said tooth and being contoured to form said smooth beveled surface when vibrated on said ground tooth.

16. The method of claim 14 including grinding said tooth with a rotary tool to form a shoulder and abrading said shoulder with said vibrating tool.

17. A method of cutting away a tooth for fitting of a dental crown of the type wherein the tooth is ground to a shoulder leaving a central core over which the crown is fitted, wherein the improvement comprises:

providing a vibrating dental tool having a shank portion adapted for connection to a source of ultrasonic vibration and a contoured portion carried by said shank portion having an abrasive carried thereon for abrading said tooth and being contoured to form said smooth beveled surface when vibrated on said ground tooth shoulder.

* * * * *